(12) United States Patent
Thovex et al.

(10) Patent No.: US 9,816,974 B2
(45) Date of Patent: Nov. 14, 2017

(54) STATION AND METHOD FOR MEASURING PARTICLE CONTAMINATION OF A TRANSPORT CARRIER FOR CONVEYING AND STORING SEMICONDUCTOR SUBSTRATES AT ATMOSPHERIC PRESSURE

(71) Applicant: ADIXEN VACUUM PRODUCTS, Annecy (FR)

(72) Inventors: Cindy Thovex, La Clusaz (FR); Nicolas Chapel, Sales (FR); Bertrand Bellet, Annecy (FR)

(73) Assignee: ADIXEN VACUUM PRODUCTS, Annecy (FR)

( * ) Notice: Subject to any disclaimer, the term of this patent is extended or adjusted under 35 U.S.C. 154(b) by 261 days.

(21) Appl. No.: 14/443,745

(22) PCT Filed: Nov. 29, 2013

(86) PCT No.: PCT/EP2013/075076
§ 371 (c)(1),
(2) Date: May 19, 2015

(87) PCT Pub. No.: WO2014/083152
PCT Pub. Date: Jun. 5, 2014

(65) Prior Publication Data
US 2015/0301007 A1    Oct. 22, 2015

(30) Foreign Application Priority Data

Nov. 30, 2012 (FR) ...................................... 12 61453

(51) Int. Cl.
*G01N 33/00* (2006.01)
*H01L 21/673* (2006.01)

(52) U.S. Cl.
CPC ....... *G01N 33/0009* (2013.01); *H01L 21/673* (2013.01); *H01L 21/67389* (2013.01)

(58) Field of Classification Search
CPC ... G01N 33/0009; H01L 21/67; H01L 31/673; H01L 21/6735; H01L 21/673
See application file for complete search history.

(56) References Cited

U.S. PATENT DOCUMENTS

2002/0029791 A1    3/2002  Matsuoka
2011/0048143 A1    3/2011  Favre et al.

FOREIGN PATENT DOCUMENTS

FR        2 930 675  A1    10/2009

OTHER PUBLICATIONS

International Search Report for PCT/EP2013/075076 dated Jan. 29, 2014 [PCT/ISA/210].

*Primary Examiner* — Erika J Villaluna
(74) *Attorney, Agent, or Firm* — Sughrue Mion, PLLC (57) ABSTRACT

The present invention relates to a method for measuring particle contamination of a transport carrier for conveying and storing semiconductor substrates at atmospheric pressure, implemented in a measuring station. The measuring method comprises:
  a step in which the measuring module (5) couples to the rigid casing (2), thereby defining a first measuring volume (V1) between the casing-measuring interface (16) and the coupled rigid casing (2) in order to measure contamination of the internal walls of the rigid casing (2); and
  a step in which the door (3) couples to the measuring module (5), thereby defining a second measuring volume (V2) between said measuring face (22) and the opposite door (3) in order to measure contamination of the door (3).

The invention also relates to an associated measuring station.

12 Claims, 7 Drawing Sheets

STATION AND METHOD FOR MEASURING PARTICLE CONTAMINATION OF A TRANSPORT CARRIER FOR CONVEYING AND STORING SEMICONDUCTOR SUBSTRATES AT ATMOSPHERIC PRESSURE

CROSS REFERENCE TO RELATED APPLICATIONS

This application is a National Stage of International Application No. PCT/EP2013/075076, filed on Nov. 29, 2013, which claims priority from French Patent Application No. 1261453, filed on Nov. 30, 2012, the contents of all of which are incorporated herein by reference in their entirety.

The present invention relates to a station for measuring particle contamination of a transport carrier for conveying and storing semiconductor substrates, such as semiconductor wafers or photomasks, at atmospheric pressure. The invention also relates to a corresponding measuring method.

Transport carriers define a confined space, at atmospheric pressure and separated from the external environment, for transporting and storing one or more substrates.

In the semiconductor fabrication industry, these carriers allow substrates to be transported from one tool to another or substrates to be stored between two fabrication steps. Mention may especially be made, by way of standardized carriers for transporting and storing wafers, of front opening carriers such as FOUPs (front opening unified pods) or FOSBs (front opening shipping boxes), bottom opening carriers such as SMIF Pods (standard mechanical interface pods), or even standardized carriers for transporting and storing photomasks, such as RSPs (reticle SMIF pods) or MRPs (multiple reticle SMIF pods).

These transport carriers are made of materials such as polycarbonate that may in certain cases concentrate contaminants, and in particular organic, amine or acid contaminants. Specifically, during fabrication of semiconductors, transport carriers are handled, which leads to the formation of polluting particles that lodge on the walls of the transport carriers and contaminate them. Particles attached to the walls of the transport carriers may then come unstuck and fall onto the substrates stored in these carriers making them unusable. This contamination may be very detrimental to the substrates. It is therefore necessary to clean these carriers. Provision is therefore made for them to be washed regularly in a liquid such as pure water. These cleaning steps are either carried out by the semiconductor substrate production fab itself, or by a company specializing in the cleaning of atmospheric transport carriers.

To determine when a carrier requires cleaning, a known method for measuring particle contamination consists in measuring the number of particles deposited on the walls of the transport carrier using a liquid particle detector. However, this method has the drawback of being time-consuming and difficult to implement in the context of industrial semiconductor fabrication. In addition, this type of process is not reproducible. Specifically, the measurement obtained depends directly on the specialist enterprise tasked with carrying out the measurement, which prevents standardized quality control procedures from being implemented. Therefore, certain particle-free transport carriers are cleaned regardless, thus needlessly decreasing production rates, whereas others, polluted with particles, continue to be used to store and/or transport semiconductor substrates, running the potential risk of substrate contamination.

Industrial groups therefore implement frequent preventive cleaning in order not to impact on substrate defectivity levels.

To prevent this, devices for measuring particle contamination of transport carriers in real time directly in the production fab are known, for example from document WO 2009/138637. The measuring device comprises a first chamber intended to take the door off the carrier, and a second chamber intended to measure particle contamination of the rigid casing of the carrier. The interface comprises a hinged injecting nozzle for directing a gas jet against the internal walls of the rigid casing, so as to detach particles in order to measure them with a particle counter. To improve the detachment of particles, provision is made to pulse the injected gas flow.

However, this measuring device does not allow the particle contamination level of the door, which is most often the most polluted wall of the transport carrier, to be inspected.

One of the aims of the present invention is therefore to provide a measuring station and a corresponding method allowing the particle contamination level of all the internal walls of an atmospheric transport carrier, including its door, to be measured.

For this purpose, one subject of the invention is a station for measuring particle contamination of a transport carrier for conveying and storing semiconductor substrates at atmospheric pressure, said transport carrier comprising a rigid casing containing an aperture and a removable door allowing the aperture to be closed, the measuring station comprising:

a controlled environment chamber comprising at least one load port capable of coupling, on the one hand, to the rigid casing, and on the other hand, to the door of the transport carrier, in order to move the door into the controlled environment chamber; and a measuring module comprising a particle measuring unit, characterized in that said measuring module comprises:

a casing-measuring interface configured to couple to the rigid casing coupled to the controlled environment chamber in the place of the door, thereby defining a first measuring volume, said casing-measuring interface comprising at least one injecting nozzle and a first sampling orifice connected to the particle measuring unit; and a hollow, door-measuring interface configured to couple to the door, thereby defining a second measuring volume between a measuring face of the measuring module and the opposite door, said measuring face comprising at least one injecting nozzle and a second sampling orifice connected to the particle measuring unit.

The hollow, door-measuring interface thus allows a confined measuring volume to be defined, into which injecting nozzles blow gas to detach particles from the door, and from which a second sampling orifice, connected to the particle measuring unit, takes a gas sample when a measurement is carried out. It is therefore possible to measure particle contamination of the door. Furthermore, the shell-like shape of the peripheral casing of the transport carrier is used to define a confined measuring volume that is separated from the controlled environment chamber.

The hollow, door-measuring interface for example has a generally frame-like shape.

The door is, for example, capable of being moved in the direction of the hollow, door-measuring interface.

The measuring module may comprise a module-moving mechanism configured to move the casing-measuring interface between a rest position and a measuring position in the coupled rigid casing.

According to one embodiment, the casing-measuring interface and the hollow, door-measuring interface are arranged back-to-back. For example, the casing-measuring interface is capable of being translated into the coupled rigid casing, and the door is capable of being translated in the direction of the hollow, door-measuring interface.

The sampling line of the particle measuring unit may comprise a valve-comprising device for selectively switching between the first and second sampling orifices. Thus, a single particle counter is used to measure both the particle contamination level of the door and the particle contamination level of the internal walls of the rigid casing, thereby allowing both the cost of the measuring station and maintenance costs to be decreased.

According to one embodiment, the casing-measuring interface comprises at least two injecting nozzles configured to direct a gas jet onto at least two separate locations on the rigid casing coupled to the controlled environment chamber, the respective orientations of the injecting nozzles being fixed relative to the coupled rigid casing.

Thus, the injecting nozzle is no longer moved to blow gas onto various zones of the internal walls of the rigid casing, as in the prior art. Instead, gas is blown through injecting nozzles that have fixed orientations, in order to detach particles and take a measurement without a moving part in the confined volume of the rigid casing, closed by the casing-measuring interface. Thus, it is ensured that gas is blown from as close as possible to the internal walls of the rigid casing, without moving the injecting nozzles during the blowing operation.

Moreover, the distance between the outlets of the injecting nozzles and the internal walls of the rigid casing is controlled and may be optimized.

In addition, the orientation of the gas jets and the value of the flow rate/pressure pair of the injecting nozzles being controlled and defined once and for all, the conditions of detachment of the particles may be reproduced identically, ensuring the reproducibility of the measurements.

The measuring station may comprise a processing unit configured to control selective injection of the gas into the injecting nozzles.

According to one embodiment, the casing-measuring interface comprises a measuring head protruding from a base of the casing-measuring interface. For example, said measuring head has a generally parallelepipedal shape, and each of the five faces of the measuring head protruding from the base of the casing-measuring interface may comprise at least one injecting nozzle. It is thus possible to selectively control injection of gas into each of the five faces of the rigid casing, and to measure, in turn, the contamination of each of the faces, thereby allowing the origin of the contamination, and a cleanliness state, to be determined with precision for each internal wall of the carrier.

The injecting nozzles may comprise injectors made of a hard material, such as ruby, sapphire, or zirconia injectors, allowing the dimensions of the injecting orifice to be defined with very high precision, thereby making good measurement reproducibility possible. In addition, injectors made of hard materials are wear resistant, thereby allowing drift in their dimensions over time to be avoided.

The injecting nozzles may, for example, be configured to direct a gas jet in at least two directions that are perpendicular to one another and perpendicular to the walls of a rigid transport carrier casing coupled to the controlled environment chamber. A gas jet confined perpendicularly to a wall improves the impact on the wall, enabling effective detachment of particles attached to the internal walls of the rigid casing.

The particle measuring unit may comprise cleaning means configured to inject a purging gas into the sampling line.

The actuators of the door-actuating mechanism and/or the module-moving mechanism may be arranged in the controlled environment chamber, and the controlled environment chamber may comprise a filtering laminar flow unit for placing the internal atmosphere of the controlled environment chamber under a laminar flow of filtered air so that any particles generated by the actuators are expelled from the measuring station.

The measuring station may comprise an electrical cabinet located beside the controlled environment chamber, said electrical cabinet housing a vacuum pump of the particle measuring unit, the various components housed in the electrical cabinet thus being prevented from contaminating the controlled environment chamber.

According to one particular embodiment, the controlled environment chamber comprises two load ports capable of coupling to a respective transport carrier. The module-moving mechanism is, for example, configured to move the casing-measuring interface between a rest position and a measuring position in one or other of the coupled rigid casings.

Another subject of the invention is a method for measuring particle contamination of a transport carrier for conveying and storing semiconductor substrates at atmospheric pressure, implemented in a measuring station such as described above, characterized in that it comprises:

a step in which the measuring module couples to the rigid casing, thereby defining a first measuring volume between the casing-measuring interface and the coupled rigid casing in order to measure contamination of the internal walls of the rigid casing; and a step in which the door couples to the measuring module, thereby defining a second measuring volume between said measuring face and the opposite door in order to measure contamination of the door.

According to one embodiment, a first interstice is left between the casing-measuring interface and the rigid casing coupled to the casing-measuring interface. The gas jet injected into the injecting nozzles is parameterized, relative to the sampled gas, to generate a leakage gas flow, through the first interstice, directed towards the exterior of the rigid casing. A second interstice is left between the hollow, door-measuring interface and the rigid casing coupled to the hollow, door-measuring interface. The gas jet injected into the injecting nozzles is parameterized, relative to the sampled gas, to generate a leakage gas flow, through the second interstice, directed towards the exterior of the hollow, door-measuring interface.

By injecting more gas than is sampled, it is ensured that neither the rigid casing nor the door are contaminated.

Thus, a rapid, automatic and reproducible measurement is obtained that furthermore provides details on the origin of the particles with respect to the internal walls of the transport carrier.

Figure 1:
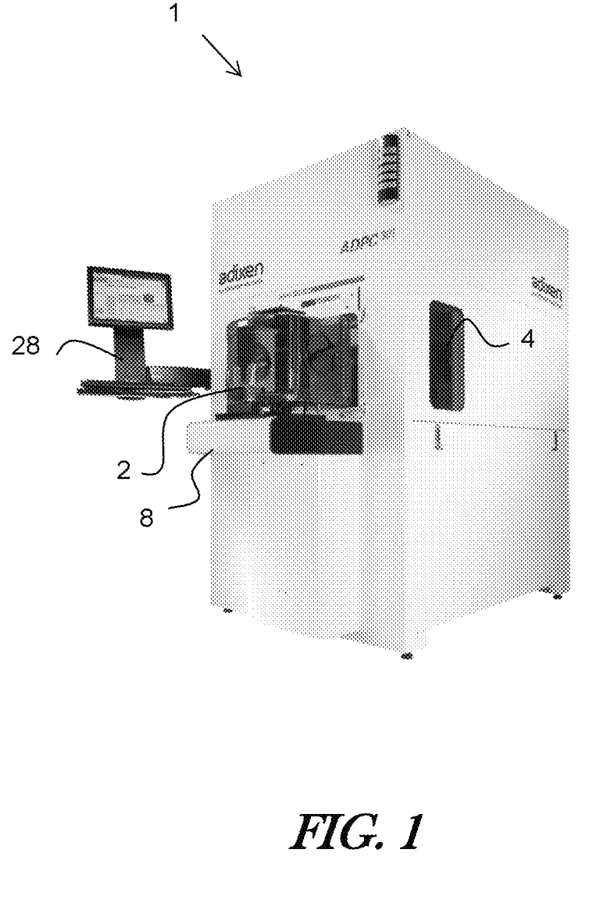
FIG. 1 shows a perspective view of a first embodiment of a station for measuring particle contamination, coupled to a transport carrier.

Other advantages and features will become apparent on reading the description of an illustrative and nonlimiting example of the present invention, and from the appended drawings in which:

FIG. 1 shows a station 1 for measuring particle contamination, coupled to a FOUP transport carrier for conveying and storing semiconductor substrates at atmospheric pressure.

Although the figures illustrate a measuring station capable of coupling to a FOUP transport carrier, the measuring station may be adapted to other types of transport carriers for conveying and storing semiconductor substrates at atmospheric pressure, such as, in particular, standardized carriers such as SMIFs, FOSBs, RSPs or MRPs.

These transport carriers have a confined air or nitrogen interior atmosphere at atmospheric pressure, i.e. at a pressure substantially equivalent to that of the operating environment of the cleanroom, but separated from the latter.

Figure 2:
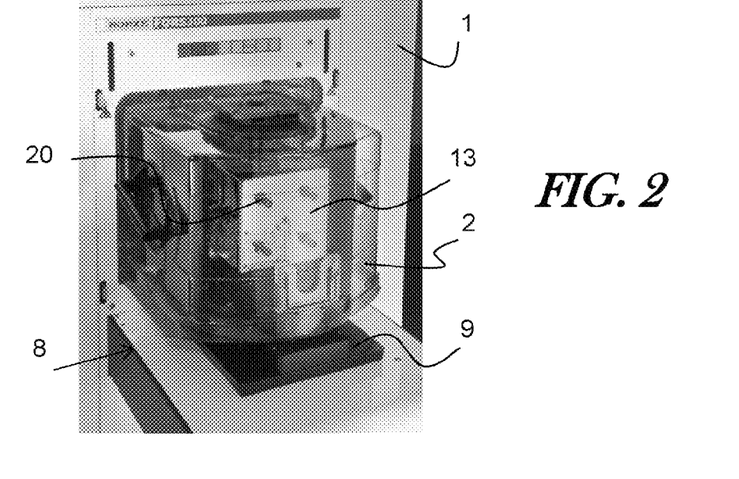
FIG. 2 shows an enlarged view of the rigid casing of the transport carrier coupled to the measuring station with the measuring module in its measuring position.
Figure 3A:
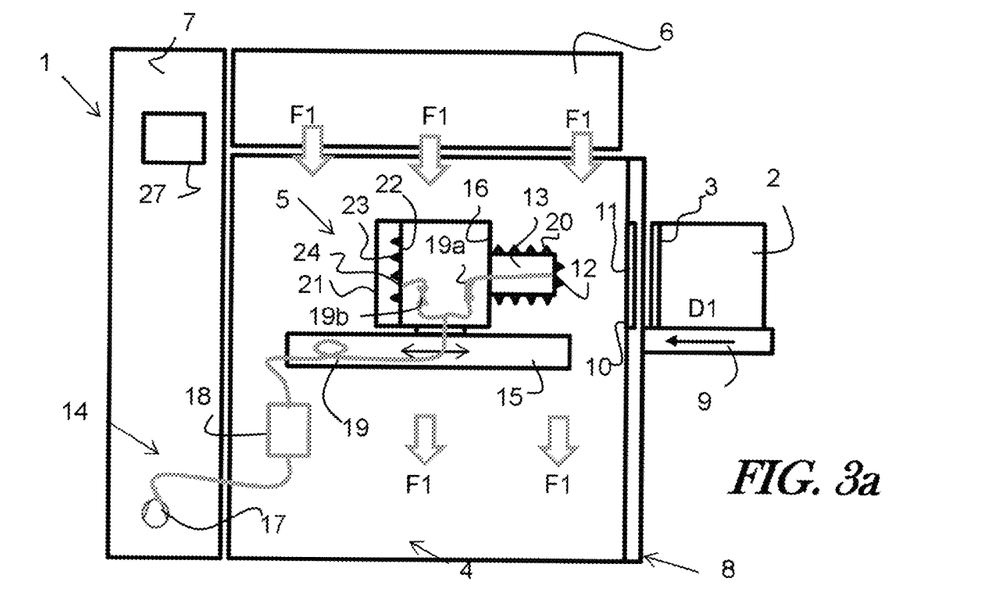
FIG. 3a shows a schematic view of a measuring station and a transport carrier.

As may be seen in FIGS. 2 and 3a, transport carriers comprise a peripheral rigid casing 2 having a general, substantially parallelepipedal shape, and contain an aperture able to be closed with a removable door 3 and dimensioned to allow substrates to be inserted and removed. The casing 2 and the door 3 are made of materials such as polycarbonate. In the case of FOUP transport carriers, the rigid casing 2 has a substantially cylindrical bottom wall. The internal side and bottom walls and the door 3 are equipped with slots for holding substrates. The carrier is relatively well sealed, but the sealing level is such that small leaks may occur through a seal arranged between the rigid casing 2 and the door 3. Certain transport carriers, especially FOUP carriers, comprise filtered gas vents in order to allow equilibrium to be reached between the pressure inside and outside the transport carrier.

For the measurements, the transport carriers are emptied of their substrates.

As may be seen in the schematic illustration in FIG. 3a, the measuring station 1 comprises a controlled environment chamber 4 and a measuring module 5.

The internal atmosphere of the controlled environment chamber 4 is at atmospheric pressure, such as defined above.

The chamber 4 is a cleanroom chamber. It is for example certified ISO 3, in accordance with standard ISO 146644-1, and forms what is called a "mini environment". For this purpose, the controlled environment chamber 4 may comprise a filtering laminar flow unit 6.

The filtering laminar flow unit 6 comprises air filters for filtering particles from the external air that penetrates into the controlled environment chamber 4. The filtering laminar flow unit 6 also comprises flow diffusers for diffusing the filtered air into a laminar flow, for example from the top of the station 1 to the bottom, as schematically shown by the arrows F1 in FIG. 3a. Furthermore, the bottom of the controlled environment chamber 4 is perforated to allow the laminar flow to sweep through. The filtering laminar flow unit 6 thus allows the internal atmosphere of the controlled environment chamber 4 to be swept with a laminar flow of filtered air in order to limit the admission of any particles possibly generated by the circulating air or by components moving in the control environment chamber 4, and to ensure their evacuation.

The measuring station 1 comprises an electrical cabinet 7 allowing all or some of the electrical components of the station to be housed and supplied with power. The electrical cabinet 7 is advantageously located beside the controlled environment chamber 4, outside of the laminar flow of filtered air, in order to prevent the controlled environment chamber 4 from being contaminated by the various components housed in the electrical cabinet 7.

The controlled environment chamber 4 comprises a front access 10 and a load port 8 arranged under the access 10.

The load port 8 is capable of coupling, on the one hand, to the rigid casing 2, and on the other hand, to the door 3 of the transport carrier in order to move the door 3 into the controlled environment chamber 4 and to place the interior of the rigid casing 2 in communication with the interior of the controlled environment chamber 4.

The load port 8 comprises a platform 9 allowing a transport carrier to be received and positioned. The platform 9 may comprise a presence sensor adapted to check whether the transport carrier model is compatible with the measuring station 1 receiving the carrier. Furthermore, in order to couple to the rigid casing 2, the platform 9 of the load port 8 comprises a docking means for, on the one hand, clamping the rigid casing 2, and on the other hand, for advancing it against the access 10 of the controlled environment chamber 4 (arrow D1 in FIG. 3a).

The load port 8 also comprises a load port door 11. The load port door 11 is substantially the same size as the door 3 of the transport carrier. The load port door 11 especially allows the access 10 of the controlled environment chamber 4 to be closed in the absence of a transport carrier. It furthermore comprises lock-actuating means for locking and unlocking locking members of the door 3.

The locking members of the door 3, known per se, for example comprise bolts borne by the door 3, which bolts are actuated via a radial or lateral sliding motion and engage with the rigid casing 2 of the transport carrier when the transport carrier is closed.

Once the locking members have been unlocked, the lock-actuating means reversibly secure the door 3 to the load port door 11. The door/door assembly 3, 11 may then be moved as one into the controlled environment chamber 4. To do this, the load port door 11 comprises a door-actuating mechanism.

Figure 3B:
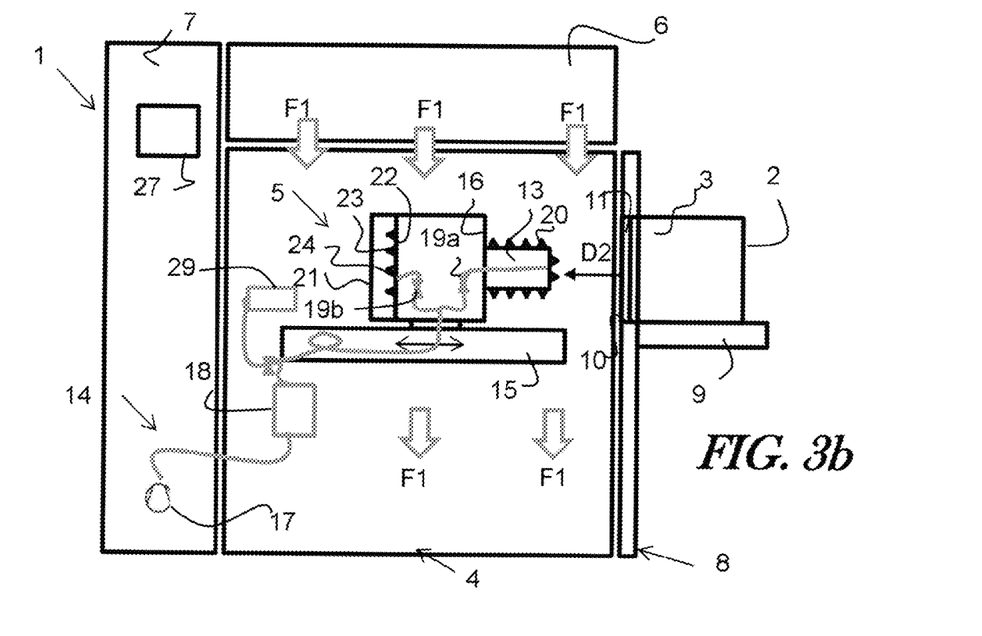
FIG. 3b shows a similar view to FIG. 3a, during a first step of the measuring method, in which step the load port of the measuring station couples to the door of the transport carrier.

The door-actuating mechanism for example comprises a first motorized linear axis (not shown) enabling a linear translation, such as a horizontal translation, as shown by the arrow D2 in FIG. 3b. These actuators are advantageously magnetic bearing actuators, in order to allow them to move without friction and therefore cleanly. The door-actuating mechanism is arranged in the controlled environment chamber 4 under the filtered laminar flow so that any particles generated by the actuator are evacuated.

The door/door assembly 3, 11 is moved out of the frontal zone of the access 10, for example to near the internal wall of the controlled environment chamber 4 opposite the access 10. According to another embodiment (not shown), the door-actuating mechanism moves the door/door assembly 3, 11 towards the bottom of the controlled environment chamber 4 rather than horizontally.

When the door 3 is moved away from the rigid casing 2, the internal volume of the rigid casing 2 is brought into communication with the internal volume of the controlled environment chamber 4.

The measuring module 5 comprises a casing-measuring interface 16 configured to couple to a rigid transport carrier casing 2 coupled to the controlled environment chamber 4, in the place of the door 2, a particle measuring unit 14, and a module-moving mechanism 15.

The casing-measuring interface 16 is equipped with at least two injecting nozzles 20 configured to direct a gas jet onto at least two separate locations on the coupled rigid casing 2, the respective orientations of the injecting nozzles 20 being fixed relative to the coupled rigid casing 2. The casing-measuring interface 16 also comprises a first sampling orifice 12 connected to the particle measuring unit 14.

The sampling orifice 12 and the injecting nozzles 20 are, for example, arranged on a measuring head 13 protruding from a base of the casing-measuring interface 16.

The injecting nozzles 20 comprise injectors made of a hard material, such as ruby, sapphire or zirconia. The injectors are hollow cylinders made of a hard material, the inside diameter of which may be defined with a very high precision (of about a few μm), this inside diameter defining the gas injection flow rate/pressure difference between the atmospheric pressure of the controlled environment chamber 4 and the inlet pressure of the gas, pair. Injectors made of a hard material are wear resistant, thereby allowing drift in their dimensions over time to be avoided, and ensuring that they can be produced very precisely, thus making good measurement reproducibility possible.

The injectors are connected to gas supply systems provided with isolating valves (not shown), passing through a housing 5a of the measuring module 5. The gas injected is an inert gas such as nitrogen. The injecting nozzles 20 are furthermore provided with particle filters in order to filter any particles polluting the injected gas.

Figure 3C:
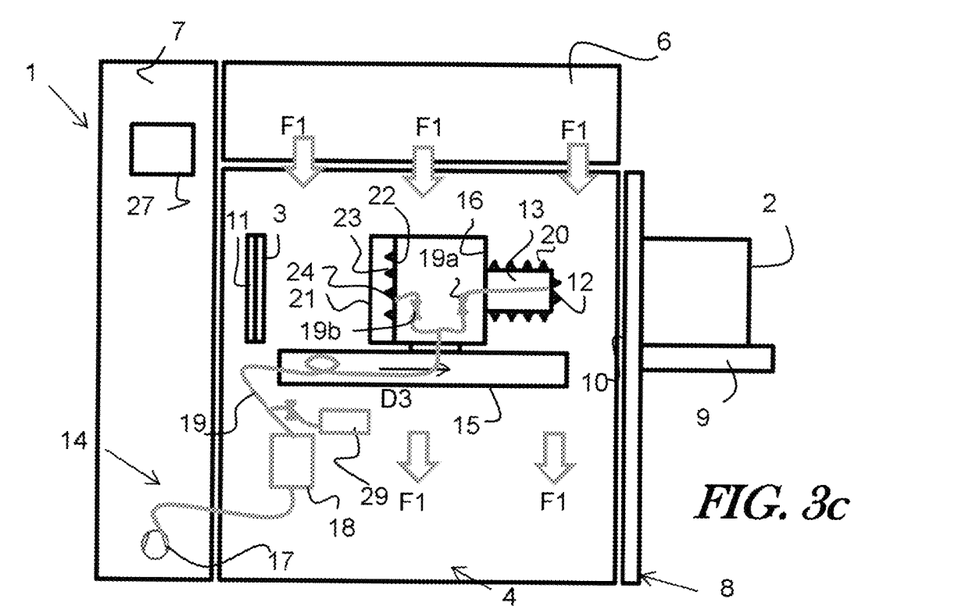
FIG. 3c shows a similar view to FIG. 3a, during a second step of the measuring method, in which step a door of the load port and the coupled door are moved into the controlled environment chamber.
Figure 3D:
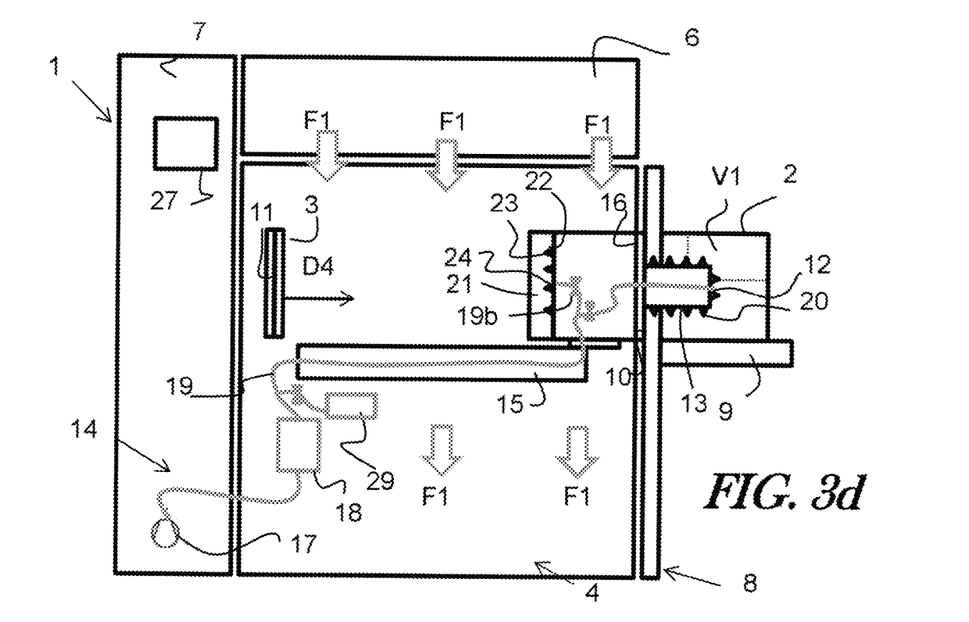
FIG. 3d shows a similar view to FIG. 3a, during a fourth step of the measuring method, in which step the casing-measuring interface is coupled to the rigid casing.

The injecting nozzles 20 are for example configured to direct a gas jet in at least two directions that are perpendicular to one another and perpendicular to the walls of the rigid casing 2 coupled to the controlled environment chamber 4 (see the example gas jets represented by the dotted lines in FIG. 3d). A gas jet confined perpendicularly to a wall improves the impact on the wall for effective detachment of particles.

The measuring head 13 for example has a general parallelepipedal shape substantially complementary to the internal shape of the rigid casing 2. Each of the five faces of the measuring head 13 protruding from the base of the casing-measuring interface 16, comprises at least one injecting nozzle 20 so as to direct a gas jet in a direction substantially orthogonal to the face of the measuring head 13. It is thus possible to individually measured each of the five faces of the rigid casing 2.

Furthermore, each face may comprise a plurality of injecting nozzles 20, configured, for example, to direct gas jets in directions that are parallel to one another.

For example, and as shown in FIG. 2, the measuring head 13 comprises four injecting nozzles 20 on each of the five protruding faces. The four injecting nozzles 20 of a face are located at the four corners of a square shape.

Figure 4:
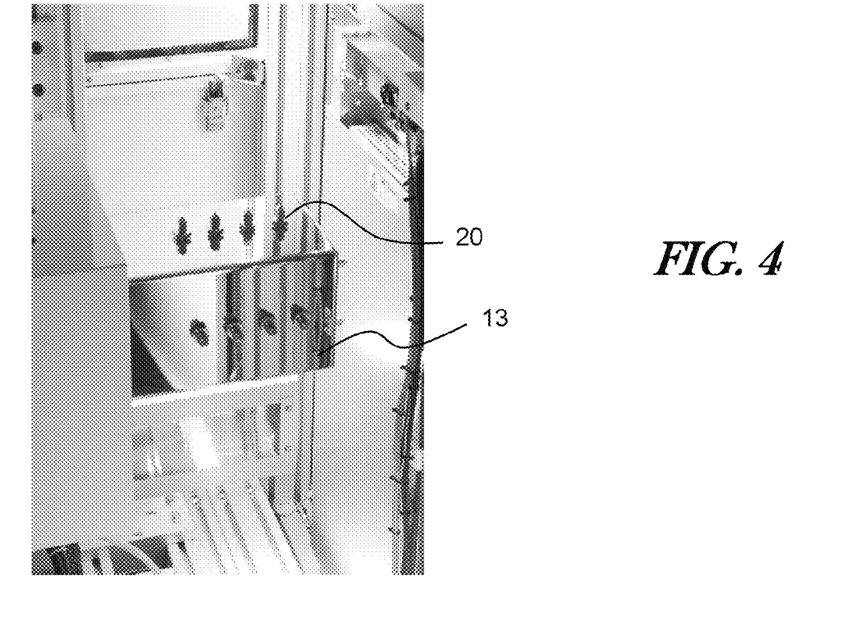
FIG. 4 shows one embodiment of a measuring head.

According to another example, shown in FIG. 4, the four injecting nozzles 20 of each face are aligned along a substantially median horizontal line.

To increase measurement reliability, it is possible, for example, to localize the gas jets to particularly critical zones of the rigid casing 2, such as the slots for holding substrates, or the corners of the rigid casing 2. It is also possible to maximize coverage of the surface of the internal wall, especially by increasing the number of injecting nozzles 20 per face.

The first sampling orifice 12 is for example housed in one of the faces of the measuring head 13.

The measuring head 13 is configured so that the distance between the outlet of an injecting nozzle 20 and the internal wall of a coupled rigid casing 2 is smaller than a few centimeters, such as comprised between 1 mm and 10 cm. In order to optimize the detachment of particles, the flow rate of the injecting nozzles 20 is for example comprised between 10 and 30 l/min, such as about 20 l/min, depending on the number of injecting nozzles 20, the flow rate decreasing as the number of injecting nozzles 20 increases. The pressure difference between the atmospheric pressure of the controlled environment chamber 4 and the inlet pressure of the gas is for example about 3 to 4 bars.

The module-moving mechanism 15 is configured to move the casing-measuring interface 16 into between a rest position (FIG. 3a) and a position for measurement of the rigid casing 2 coupled to the controlled environment chamber 4 (FIG. 3d). The module-moving mechanism 15 comprises a second motorized linear axis enabling, for example, two linear translations, such as a horizontal translation, as shown by the arrow D3 in FIG. 3c, and a vertical translation for shifting the measuring head 13 out of a frontal zone of the access 10 during the movement of the door 3 towards/away from the rigid casing 2. As for the door-actuating mechanism, the actuator of the module-moving mechanism 15 is advantageously a magnetic bearing actuator, and is placed in the controlled environment chamber 4 under the laminar flow of filtered air.

The measuring head 13 protrudes from the base of the casing-measuring interface 16 in the direction of the access 10 of the controlled environment chamber 4. The base of the casing-measuring interface 16 is substantially the same shape and size as a transport carrier door 3, in order to be easily coupled to a rigid transport carrier casing 2 in the place of the door 3. The measuring head 13 is for example securely fastened to the centre of the base of the casing-measuring interface 16.

When the casing-measuring interface 16 is moved into the rigid casing 2 coupled to the controlled environment chamber 4, i.e. into the measuring position, the casing-measuring interface 16 closes the rigid casing 2 in the place of the door 3, thereby defining a first measuring volume V1 (FIG. 3d). The measuring head 13 is received into this first measuring volume V1, thereby bringing the interior of the rigid casing 2 into communication with the first sampling orifice 12 connected to the particle measuring unit 14, and with the injecting nozzles 20. Thus, the shell-like shape of the peripheral casing of the transport carrier is used to define a first measuring volume V1 between the rigid casing 2 and the casing-measuring interface 16. The measurement is then carried out in this confined first measuring volume V1 separated from the rest of the measuring station 1.

The casing-measuring interface 16 does not sealably close the rigid casing 2, a small first interstice being left between the two for the passage of a leakage flow. The injection flow of gas injected into the injecting nozzles 20 is parameterized to create a slight overpressure in the first measuring volume V1 relative to the external environment, thus promoting gas flow towards the exterior through the first interstice, thereby reducing the risk of particle contamination.

The particle measuring unit 14 for example comprises a vacuum pump 17, a particle counter 18 connected upstream of the vacuum pump 17, and a sampling line 19 upstream of the particle counter 18, as illustrated in FIG. 3a. The vacuum pump 17 is for example located in the electrical cabinet 7.

The sampling line 19 is connected, at its end, to the first sampling orifice 12 of the measuring head 13. The sampling line 19 may comprise a first isolating valve 19a arranged between the first sampling orifice 12 and the particle counter 18. The sampling line 19 is sufficiently flexible and long to allow the measuring head 13 to move back and forth. The particle measuring unit 14 may for example comprise a cable chain for holding and guiding the sampling line 19. The particle counter 18 is, for example, housed in the controlled environment chamber 4, as close as possible to the sampling orifice 12 in order to limit the length of the sampling line 19 connected to the particle counter 18.

Furthermore, the particle measuring unit 14 may comprise cleaning means 29 configured to inject a purging gas into the sampling line 19 in order to purge particles that may possibly have lodged therein.

The gas sample is taken from the first measuring volume V1 of the rigid casing 2 coupled to the casing-measuring interface 16 via suction through the first sampling orifice 12 of the measuring head 13. The number of particles contained in the gas sample is determined by the particle counter 18. The particle counter 18 is for example an aerosol particle counter, i.e. it allows quantitative information to be obtained from particles suspended in a gaseous environment. It is for example based on laser technology. The pumping flow of the vacuum pump 17 is for example about 1.7 m$^3$/h.

The positioning means, the means for checking the transport carrier model, the lock-actuating means, the door-actuating mechanisms of the load port, and the gas-injecting means are controlled by a processing unit 27 of the measuring station 1. The processing unit 27 is furthermore configured to control selective injection of the gas into the injecting nozzles 20. The processing unit 27 is connected to a user interface 28, for example especially comprising a screen and a keyboard, as may be seen in FIG. 1.

The measuring station 1 is also designed to measure the door 3 of the transport carrier.

Figure 3E:
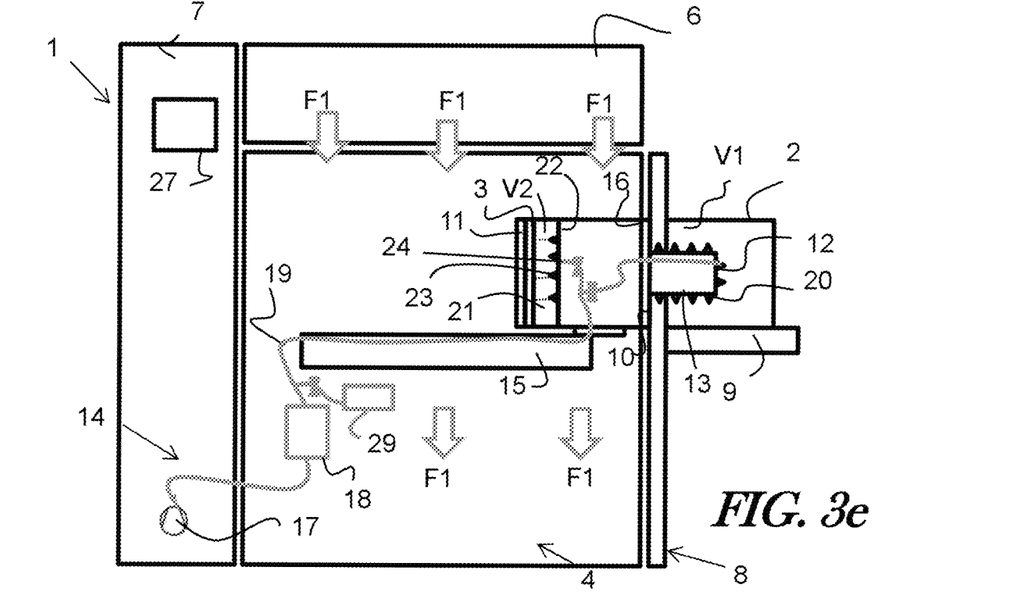
FIG. 3e shows a similar view to FIG. 3a, during a seventh step of the measuring method, in which step the door is coupled to the measuring module.
Figure 5:
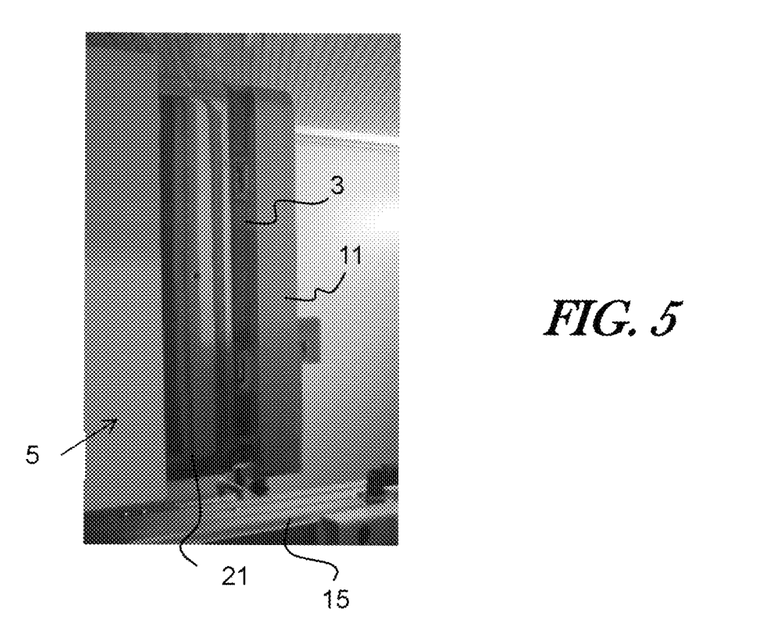
FIG. 5 shows a side view of the door sandwiched between a hollow, door-measuring interface and the door of the load port.

To do this, the measuring module 5 comprises a hollow, door-measuring interface 21 configured to couple to the door 3, thereby defining a second measuring volume V2 between a measuring face 22 of the measuring module 5 and the opposite door 3 (FIGS. 3e and 5). The door-actuating mechanism of the load port 8 is for example capable of moving the door 3 in the direction of the hollow, door-measuring interface 21 after the measuring head 13 has been moved into the rigid casing 2.

The measuring face 22 comprises at least one injecting nozzle 23 and a second sampling orifice 24. The measuring face 22 for example comprises four injecting nozzles 23. The hollow, door-measuring interface 21 thus brings the interior of the second measuring volume V2 into communication with the second sampling orifice 24 connected to the particle measuring unit 14, and with the injecting nozzles 23.

Given that the door 3 does not per se allow a volume portion permitting detached particles to be measured to be confined, it is the hollow, door-measuring interface 21 that is adapted to define a second measuring volume V2 into which the injecting nozzles 23 blow gas to detach particles from the door 3, and from which a second sampling orifice 24, connected to the particle measuring unit 14, takes the gas sample when a measurement is carried out (FIG. 3e).

The hollow, door-measuring interface 21 for example has a generally frame-like shape the peripheral dimensions of which are substantially equivalent to those of a door 3, and the thickness of which is substantially equivalent to the optimal distance between the outlet of an injecting nozzle 20 and the internal wall of a coupled rigid casing 2. The optimal distance is about a few centimeters, such as comprised between 1 and 10 cm. The second measuring volume V2 is thus a volume that is about one fifth as large as the internal volume of the transport carrier.

The injecting nozzles 23 are similar to the injecting nozzles 20 of the measuring head 13 and are, for example, configured to direct a gas jet in a direction substantially orthogonal to the measuring face 22 (see the example gas jets represented by the dotted lines in FIG. 3e).

The hollow, door-measuring interface 21 does not sealably close the door 3, a small second interstice being left between the two for the passage of a leakage flow. The injection flow of gas injected into the injecting nozzles 20 is parameterized to create a slight overpressure in the second measuring volume V2 relative to the external environment, thus promoting gas flow towards the exterior through the second interstice, thereby reducing the risk of particle contamination.

The casing-measuring interface 16 and the hollow, door-measuring interface 21 are, for example, arranged back-to-back. The measuring head 13 is capable of being translated into the coupled rigid casing 2, and the door 3 is capable of being translated in the direction of the hollow, door-measuring interface 21.

The sampling line 19 comprises a valve-comprising device for selectively switching between the first and second sampling orifices 12, 24 (FIG. 3a).

The valve-comprising device for example comprises a first isolating valve 19a arranged between the first sampling orifice 12 and the particle counter 18, and a second isolating valve 19b arranged between the second sampling orifice 24 and the particle counter 18. The first and second isolating valves 19a, 19b may be controlled by the processing unit 27 in order to measure selectively the door 3 of the transport carrier or one of the internal walls of the rigid casing 2. Thus, a single particle counter 18 is used to measure both the door 3 and the internal walls of the rigid casing 2. According to another embodiment, the valve-comprising device comprises a three-way valve.

In the rest position, the measuring module 5 is arranged in the controlled environment chamber 4 the access 10 of which is closed by the load port door 11 (FIG. 3a).

Next, when an operator or a robot places a transport carrier on the platform 9 of the load port 8, the load port 8 positions and checks the model of the transport carrier, then clamps the rigid casing 2 of the carrier and advances it against the access 10 of the controlled environment chamber 4 (arrow D1 in FIG. 3a).

The lock-actuating means of the load port door 11 then unlock the locking members of the door 3 and secure the door 3 to the load port door 11 (first step, FIG. 3*b*).

The door/door assembly 3-11 is then moved into the controlled environment chamber 4 away from the access 10 (arrow D1 in FIG. 3*b*), bringing the internal volume of the rigid casing 2 into communication with the internal volume of the controlled environment chamber 4 (second step, FIG. 3*c*). The measuring station 1 may comprise an interlock sensor making it possible to verify that the rigid casing 2 has indeed been emptied of its substrates, after the transport carrier has been opened.

In a third step, the casing-measuring interface 16 is moved in the direction of the rigid casing 2.

In a fourth step, the casing-measuring interface 16 couples to the rigid casing 2 in the place of the door 3, in the measuring position. In the coupled state, the measuring head 13 is immobilized in the first measuring volume V1 defined by the casing-measuring interface 16 and the coupled rigid casing 2. This first measuring volume V1 is therefore in communication, on the one hand, with the first sampling orifice 12 housed in the measuring head 13 and connected to the particle measuring unit 14, and on the other hand, with the injecting nozzles 20 of the measuring head 13 (FIG. 3*d*).

In a fifth step, a gas jet is injected simultaneously into all the injecting nozzles 20 of a given orientation. For example, a gas jet is injected into the four injecting nozzles 20 of a given face of the measuring head 13. The gas jet detaches a sample of the particles present on the internal walls of the coupled rigid casing 2. The distance between the outlets of the injecting nozzles 20 and the internal walls is controlled (in particular because of the dimensions of the measuring head 13), thereby allowing particles to be reproducibly detached from one transport carrier to another.

Gas is sampled from the first measuring volume V1 via suction through the sampling line 19. The number of particles contained in the gas sample is determined continuously by the particle counter 18.

The injection gas flow creates a slight overpressure in the first measuring volume V1 relative to the external environment, thus promoting gas flow towards the exterior through the first interstice between the casing-measuring interface 16 and the rigid casing 2, thereby reducing the risk of particle contamination of the rigid casing 2.

Next, the measuring operation is reiterated for the injecting nozzles 20 of given orientation on each face of the measuring head 13.

The processing unit 27 informs the user of the cleanliness state of the transport carrier face by face.

Once the casing-measuring interface 16 has been coupled to the rigid casing 2, the load port door 11 and the coupled door 3 are moved in the direction of the hollow, door-measuring interface 21 by the action of the door-actuating mechanism (sixth step, arrow D4 in FIG. 3*d*).

Next, in a seventh step, the door 3 couples to the measuring module 5, thereby defining a second measuring volume V2 between a measuring face of the measuring module 5 and the opposite door 3 (FIG. 3*e*). In the coupled state, the hollow, door-measuring interface 21 is immobilized against the measuring face 22. The second measuring volume V2 is therefore in communication, on the one hand, with the second sampling orifice 24 housed in the measuring face 22 and connected to the particle measuring unit 14, and on the other hand, with the injecting nozzles 23 of the measuring face 22. The seventh step may be performed consecutively to the fourth step.

In an eighth step, the injecting nozzles 23 inject a gas jet in the direction of the door 3. The gas jet detaches a sample of the particles present on the door 3. The distance between the outlets of the injecting nozzles 23 and the door 3 is controlled, thereby allowing particles to be reproducibly detached from one transport carrier to another.

Gas is sampled from the second measuring volume V2 via suction through the sampling line 19 after the first isolating valve 19*a* has been closed and the second isolating valve 19*b* has been opened. The number of particles contained in the gas sample is determined continuously by the particle counter 18. The injection gas flow creates a slight overpressure in the second measuring volume V2 relative to the external environment, thus promoting gas flow towards the exterior through the second interstice between the hollow, door-measuring interface 21 and the door 3, thereby reducing the risk of particle contamination.

The processing unit 27 informs the user of the cleanliness state of the transport carrier, including the door 3, face by face.

Once the measurements have finished, the door/door assembly 3, 11 is moved away from the hollow, door-measuring interface 21, the measuring head 13 is removed from the rigid casing 2, and the transport carrier is reclosed, either in order to be sent for cleaning, or in order to continue to be used for transporting and conveying, depending on its cleanliness state.

Figure 6:
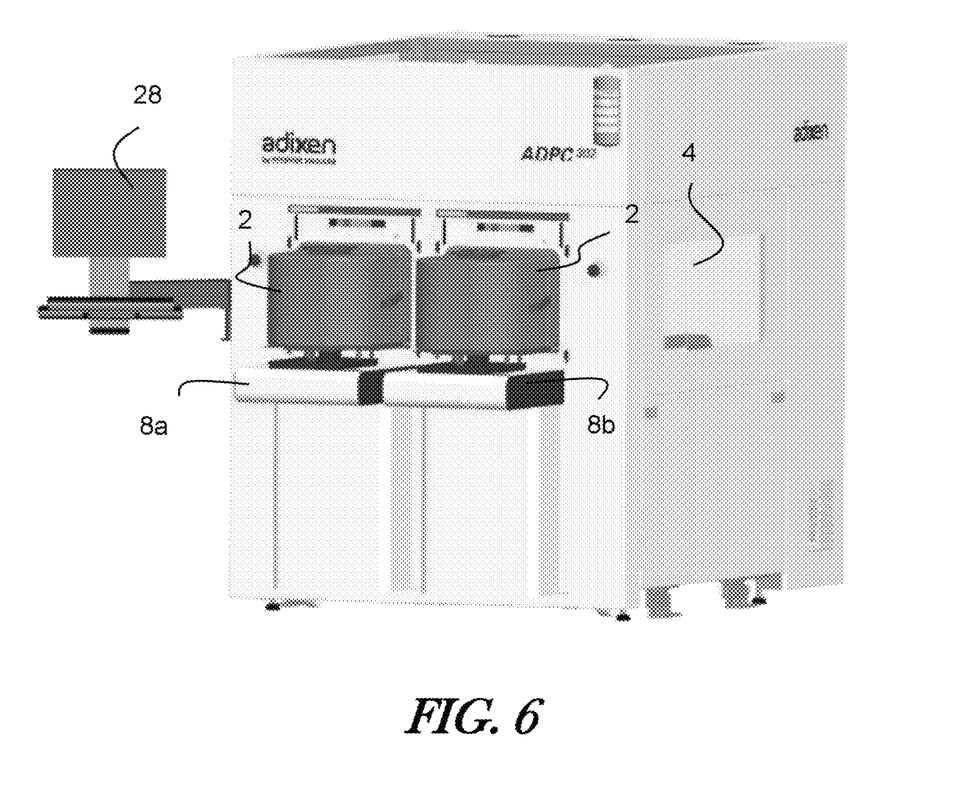
FIG. 6 shows a perspective view of a second embodiment of a station for measuring particle contamination.
Figure 7:
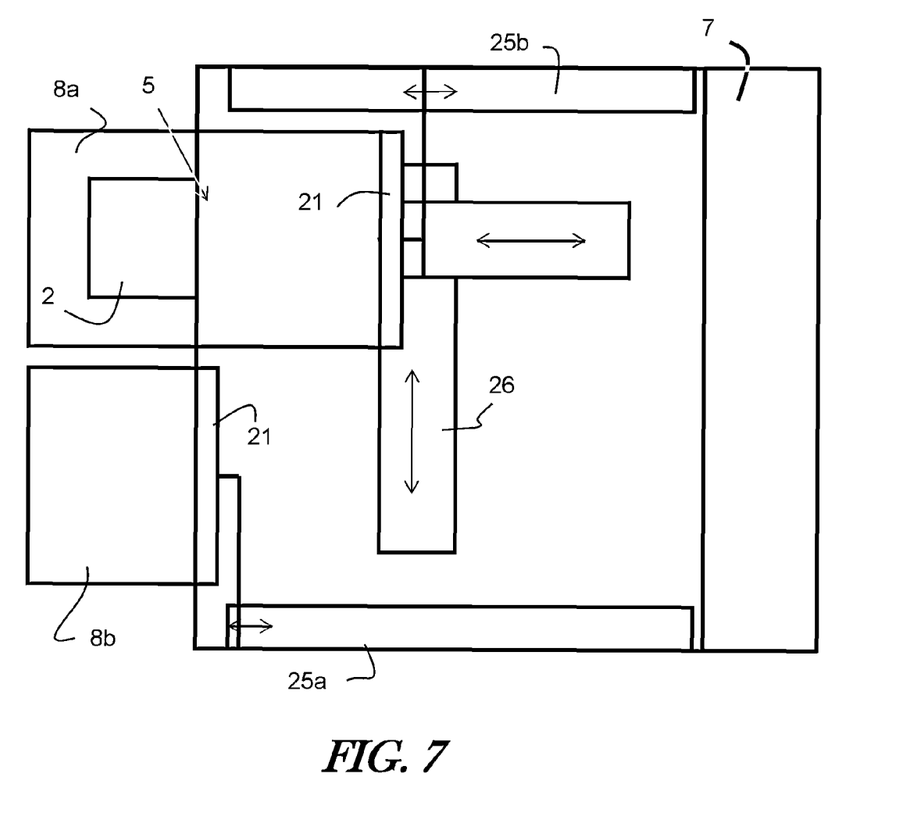
FIG. 7 shows a schematic view of the particle-measuring station in FIG. 6.

According to a second embodiment of the measuring station, shown in FIGS. 6 and 7, the controlled environment chamber 4 comprises two load ports 8*a*, 8*b* capable of coupling to respective transport carriers.

Each load port 8*a*, 8*b* comprises its own door-actuating mechanism 25*a*, 25*b*.

The module-moving mechanism 26 is configured to move the measuring head 13 into the measuring position in one or other of the coupled rigid casings 2. To do this, the module-moving mechanism 26 for example allows the measuring head 13 to be shifted laterally with respect to its axial movement in the controlled environment chamber 4. The measuring head 13 may thus be shifted from the access 10 of the controlled environment chamber 4 in order to clear the way for the door-actuating mechanism 25*a* or 25*b*.

The invention claimed is:

1. Station for measuring particle contamination of a transport carrier for conveying and storing semiconductor substrates at atmospheric pressure, said transport carrier comprising a rigid casing (2) containing an aperture and a removable door (3) allowing the aperture to be closed, the measuring station comprising:

a controlled environment chamber (4) comprising at least one load port (8) capable of coupling to the rigid casing (2) or to the door (3) of the transport carrier, in order to move the door (3) into the controlled environment chamber (4); and a measuring module (5) comprising a particle measuring unit (14), characterized in that said measuring module (5) comprises:

a casing-measuring interface (16) configured to couple to the rigid casing (2) coupled to the controlled environment chamber (4) in the place of the door (3), thereby defining a first measuring volume (V1), said casing-measuring interface (16) comprising at least one injecting nozzle (20) and a first sampling orifice (12) connected to the particle measuring unit (14); and a hollow, door-measuring interface (21) configured to couple to the door (3), thereby defining a second measuring volume (V2) between a measuring face (22) of the measuring module (5) and the opposite door (3), said measuring face (22) comprising at least one injecting nozzle (23) and a second sampling orifice (24) connected to the particle measuring unit (14).

2. Measuring station according to claim 1, characterized in that the hollow, door-measuring interface (21) has a generally frame-like shape.

3. Measuring station according to claim 1, characterized in that the door (3) is capable of being moved in the direction of the hollow, door-measuring interface (21).

4. Measuring station according to claim 1, characterized in that the measuring module (5) comprises a module-moving mechanism (15; 26) configured to move the casing-measuring interface (16) between a rest position and a measuring position in the coupled rigid casing (2).

5. Measuring station according to claim 3, characterized in that the measuring module (5) comprises a module-moving mechanism (15; 26) configured to move the casing-measuring interface (16) between a rest position and a measuring position in the coupled rigid casing (2), and further characterized in that the casing-measuring interface (16) and the hollow, door-measuring interface (21) are arranged adjacent to each other, in that the casing-measuring interface (16) is capable of being translated into the coupled rigid casing (2), and in that the door (3) is capable of being translated in the direction of the hollow, door-measuring interface (21).

6. Measuring station according to claim 1, characterized in that the sampling line (19) of the particle measuring unit (14) comprises a valve-comprising device (29a, 29b) for selectively switching between the first and second sampling orifices (12, 24).

7. Measuring station according to claim 1, characterized in that the casing-measuring interface (16) comprises at least two injecting nozzles (20) configured to direct a gas jet onto at least two separate locations on the rigid casing (2) coupled to the controlled environment chamber (4), the respective orientations of the injecting nozzles (20) being fixed relative to the coupled rigid casing (2).

8. Measuring station according to claim 7, characterized in that it comprises a processing unit (27) configured to control selective injection of the gas into the injecting nozzles (20, 23).

9. Measuring station according to claim 1, characterized in that the casing-measuring interface (16) comprises a measuring head (13) protruding from a base of the casing-measuring interface (16).

10. Measuring station according to claim 9, characterized in that said measuring head (13) has a generally parallel-epipedal shape with five faces, and in that each of the five faces of the measuring head (13) protruding from the base of the casing-measuring interface (16) comprises at least one injecting nozzle (20).

11. Method for measuring particle contamination of a transport carrier for conveying and storing semiconductor substrates at atmospheric pressure, implemented in a measuring station according to claim 1, characterized in that it comprises:
    a step in which the measuring module (5) couples to the rigid casing (2), thereby defining a first measuring volume (V1) between the casing-measuring interface (16) and the coupled rigid casing (2) in order to measure contamination of the internal walls of the rigid casing (2); and
    a step in which the door (3) couples to the measuring module (5), thereby defining a second measuring volume (V2) between said measuring face (22) and the opposite door (3) in order to measure contamination of the door (3).

12. Measuring method according to claim 11, characterized in that a first interstice is left between the casing-measuring interface (16) and the rigid casing (2) coupled to the casing-measuring interface (16), the gas jet injected into the injecting nozzles (20) being parameterized to generate a leakage gas flow, through the first interstice, directed towards the exterior of the rigid casing (2), and in that a second interstice is left between the hollow, door-measuring interface (21) and the rigid casing (2) coupled to the hollow, door-measuring interface (21), the gas jet injected into the injecting nozzles (23) being parameterized to generate a leakage gas flow, through the second interstice, directed towards the exterior of the hollow, door-measuring interface (21).

* * * * *